United States Patent
Wolz

(10) Patent No.: US 6,428,725 B1
(45) Date of Patent: Aug. 6, 2002

(54) METHOD FOR PRODUCING COMPLETELY CERAMIC STRUCTURES IN THE FIELD OF DENTISTRY

(76) Inventor: Stefan Wolz, Am Roessler Pfad 26, D-55566 Bad Sobernheim (DE)

( * ) Notice: Subject to any disclaimer, the term of this patent is extended or adjusted under 35 U.S.C. 154(b) by 0 days.

(21) Appl. No.: 09/600,328
(22) PCT Filed: Jan. 14, 1999
(86) PCT No.: PCT/DE99/00106
§ 371 (c)(1),
(2), (4) Date: Aug. 25, 2000
(87) PCT Pub. No.: WO99/35994
PCT Pub. Date: Jul. 22, 1999

(30) Foreign Application Priority Data

| | | |
|---|---|---|
| Jan. 16, 1998 | (DE) | 198 01 532 |
| Jan. 16, 1998 | (DE) | 198 01 530 |
| Jan. 16, 1998 | (DE) | 198 01 534 |
| Mar. 23, 1998 | (DE) | 198 12 664 |
| Apr. 15, 1998 | (DE) | 198 16 546 |
| Sep. 9, 1998 | (DE) | 198 41 075 |
| Nov. 16, 1998 | (DE) | 198 52 740 |

(51) Int. Cl.$^7$ .............................. A61C 13/00
(52) U.S. Cl. ........................ 264/16; 264/636
(58) Field of Search .................... 264/16, 636

(56) References Cited

FOREIGN PATENT DOCUMENTS

| | | |
|---|---|---|
| EP | 0 241 384 | 10/1987 |
| EP | 0 701 808 | 3/1996 |
| FR | 2 640 495 | 6/1990 |
| WO | WO 94/21214 | 9/1994 |
| WO | WO 97/35531 | 10/1997 |

OTHER PUBLICATIONS

Principles of Ceramics Processing by Reed, John Wiley & Sons, 1995, p. 574.*

* cited by examiner

Primary Examiner—Christopher A. Fiorilla
(74) Attorney, Agent, or Firm—Foley & Lardner

(57) ABSTRACT

The invention relates to a method for producing crowns etc. by producing a frame, for example, made of alumina, whereby a film (6) is shrink-fitted on the die (3) of a working model. The film (6) is provided with a slip and the slip is baked on a frame after the film is removed. In order to accelerate the method and to avoid the loss of materials, the die (3) is placed on a rotatable shaft (2). The slip is deposited with a tool (5). A drying process using a hot air dryer (7) is carried out during and/or after depositing the slip. This method can also be carried out in a CNC machine with which the veneer ceramic is successively deposited. A separating agent similar to lipstick can be deposited in place of the film (6). Said separating agent melts at temperatures greater than 45 DEG C. when the spacer function is not used. The invention also relates to a crease-free shrink-fitting of the film (6). In addition, the invention shows how the infiltration itself can result in the ceramic furnace, whereby the frame lies on a base which absorbs the excess glass. The invention also relates to a dosing device for slip with which the slip is to be dosed on the shrink-fitted film in a uniform consistency.

11 Claims, 4 Drawing Sheets

METHOD FOR PRODUCING COMPLETELY CERAMIC STRUCTURES IN THE FIELD OF DENTISTRY

This application is a 371 of PCT/DE99/06106 filed Jan. 14, 1999.

BACKGROUND OF THE INVENTION

From WO 97/35531 is known a method for the production of a frame for inlays, crowns and bridges in dentistry. In the case of this method, the frames are produced e.g. from alumina in that on the die of a working model a film is shrink-fitted, the shrink-fitted film is provided with a slip from the corresponding material, e.g. alumina, and then the film is removed from the working model and baked with the slip present thereon. In the case of the baking of the ceramic mass, the shrink-fitted foil burns and the frame is obtained, e.g. in the form of a small cap. Thereafter usually follows the infiltration of the small cap with a glass mass. On the so produced small cap subsequently follows the usual build-up of the facing ceramic.

The tooth replacement produced according to this method is absolutely metal-free and thus biocompatible and achieves the strength values of metal composite ceramics. Because of the simplicity of the production and of the small material costs, a valuable tooth replacement can, therefore, be made available for broad sections of the population.

Although with this method there is involved a saving of work of the order of 70–80% in comparison with the method known from EP-A-0241384, according to the invention it is possible again to shorten each individual working step, wherewith a qualatitive improvement is also achieved which is explained in more detail in the following.

BRIEF DESCRIPTION OF THE SEVERAL VIEWS OF THE DRAWINGS

On the basis of the drawings, the steps according to the invention are explained as are claimed in the patent claims.

There are shown.

DETAILED DESCRIPTION OF THE PREFERRED EMBODIMENTS

In the case of the known methods, the application of the slip hitherto took place with a brush. This had the result that, by dropping off of the slip from the film, material masses result. Before the slip is baked, it must, furthermore, be gently dried on the film. Hitherto, this was ensured by a corresponding holding time in the air.

Figure 1:
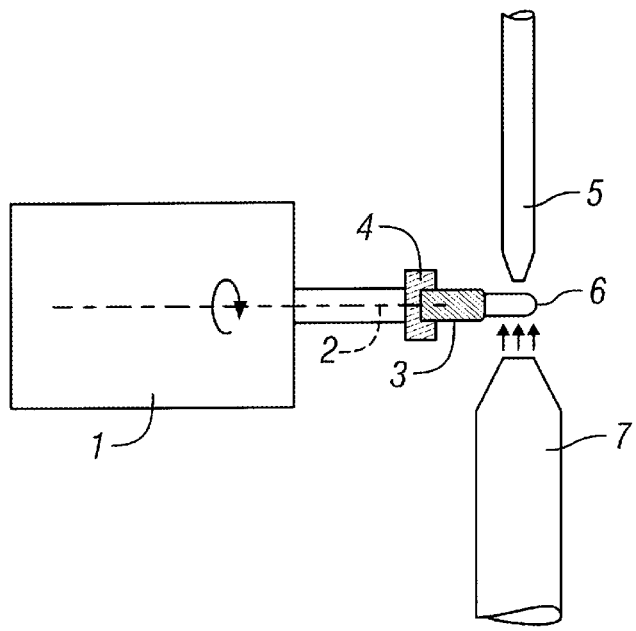
FIG. 1 a device for the application of a slip on a shrink-fitted film.

Therefore, it is one aspect of the invention to accelerate the known process without material loss which is explained in more detail in the following on the basis of FIG. 1.

The motor 1 drives a shaft 2 and can be regulated down to a speed of rotation of about one rotation per minute. On the top of the shaft 2, the die 3, usually a gypsum die of the working model, is fixed with an adhesive wax 4. In the case of the sticking in of the die 3 into the adhesive wax 4, care is to be taken that the die is applied centered as well as possible with regard to the axis of rotation of the shaft, which simplifies the application of the slip.

On the preparation of the die 3 is shrink-fitted a film 6. In order that a crease-free shrink fitting is achieved, it is expedient so to shrink-fit the film as is later explained on the basis of FIG. 3.

Figure 4:
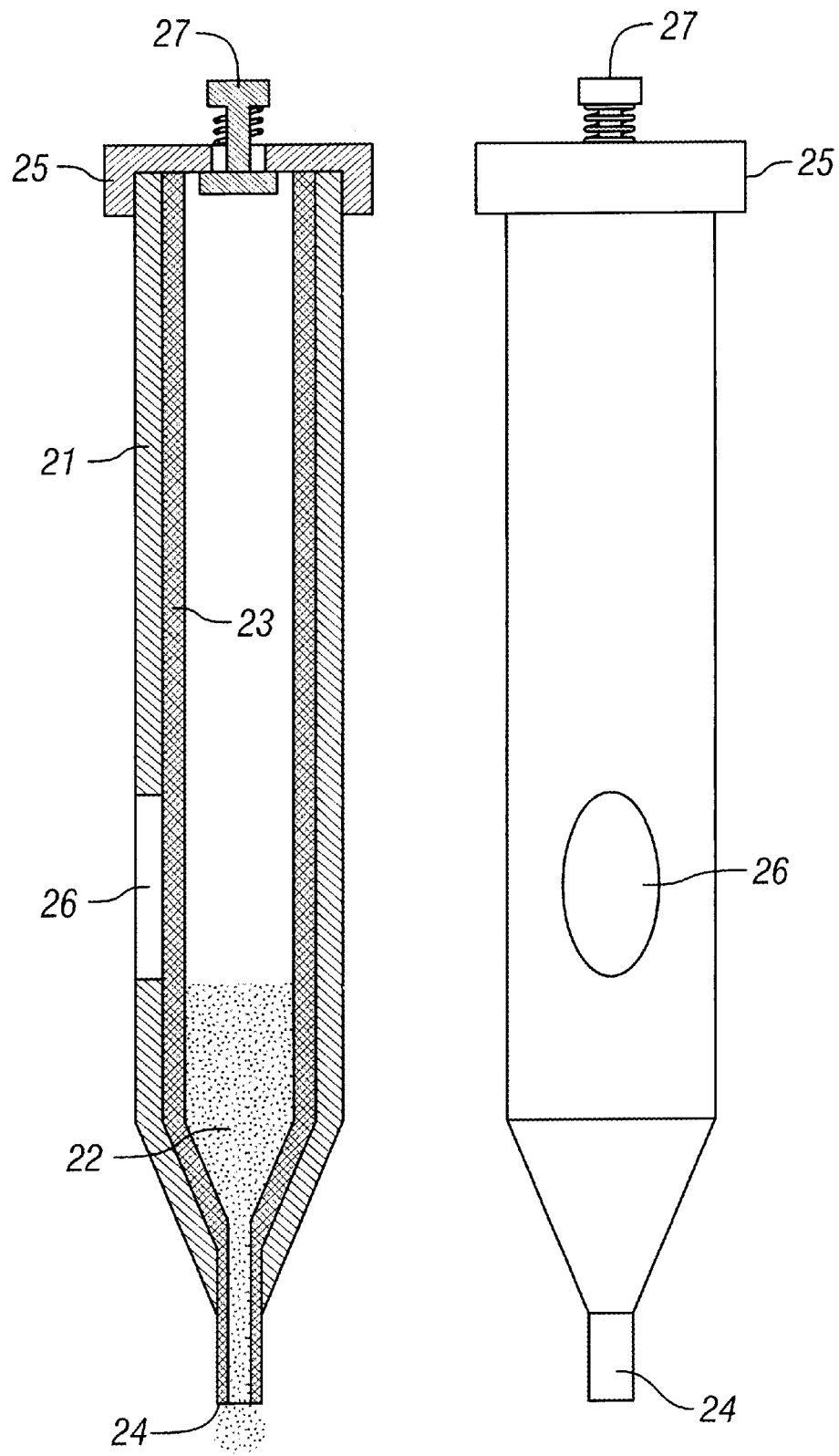
FIG. 4 a device for the application of slip or other ceramic mass in cross-section and plan view.

With the help of the tool 5, for example of a brush, the slip is applied to the film 6. It is of especial advantage when an application is used as is shown in FIG. 4. During and/or after the application of the slip, the slip is dried with a gas which is warmed above ambient temperature. For this purpose, a blow drier 7 is expediently used, the air emission temperature of which can be regulated. During the slip application, an air temperature of 25° C. to maximum 40° C. has proved useful.

The blowing on of the slip with warmed air accelerates the drying procedure and makes possible a uniform drying of the slip mass which acts positively on the frame of the baked ceramic material.

After the slip is dried on, the film 6 must be removed from the die 3. For this purpose, the blow drier temperature is increased to 80–120° C. which leads to the melting of a separating layer which is present between the film 6 and the preparation of the die 3. A simple pulling off of the film is thus ensured.

The film with slip present thereon is subsequently baked, whereby the plastic material of the film is burnt residue-free. After the so-called infiltration of the baked small cap and the usual working up, the build up of the facing ceramic can take place. From the above statements, it can also be seen that this method can be integrated without difficulty in the automated process according to FIG. 2 which is described in the following.

Figure 2:
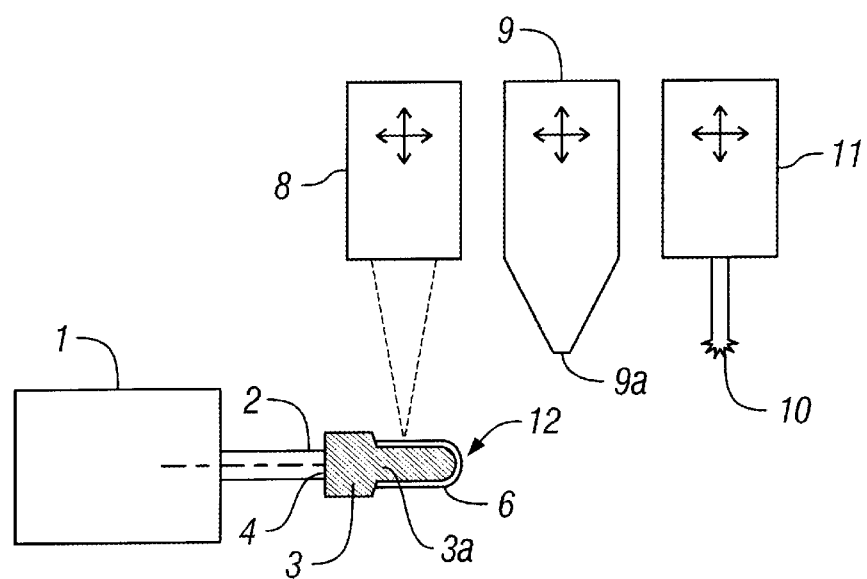
FIG. 2 a CNC machine with which, besides the slip, the facing ceramic can also be applied.

In FIG. 2, 1 indicates the motor of a Computer Numerical Control ("CNC") milling machine which sets a shaft 2 in rotation. On the end of the shaft is fixed a swan die 3 of a working model which has a preparation 3a which, according to form, agrees with the tooth stump of a patient or an implant. The tooth stump 3 is expediently fixed with an adhesive wax 4 on the shaft 2, whereby a certain form fitting between the end of the shaft 2 and the sawn die can be helpful. On to the preparation is shrink-fitted a shrink film 6 in a crease-free manner. Instead of the film, the application of a lipstick-like separation agent is also possible. However, for the purpose of simplicity, in the following the invention is only described according to the film method.

As first step in the CNC process, the surface structure of the film shrink-fitted over the object is first scanned and numerically stored. As is usual in the case of modern CNC machines, this takes place by means of a laser 8. However, a mechanical scanning is also possible.

Subsequently, there takes place the application of a slip by means of a pipette-like application device 9 which is described in more detail in FIG. 4. The outlet tip 9a is hereby passed at a close distance over the rotating film 6, whereby the distance of the outlet tip 9a to the surface of the film is numerically controlled by the previously stored values of the surface profile. The speed of rotation of the shaft 2 and the speed of emergence of the slip at the tip 9a are hereby so synchronised with one another that a continuous material flow from the tip 9a to the surface of the film is ensured. By means of these measures, the small cap already possesses in this state of the method substantially the desired wall thickness.

As next process step, there takes place the milling off of the excess material by the numerically controlled milling head 10 with a milling tool 11. The milling out of a contour in dental technology by means of a CNC milling machine is admittedly itself not new but this takes place in principle in the case of the prior art by milling out from the complete article. However, in the case of the present invention, by means of the controlled slip application, the volume to be milled off is already reduced to a minimum which makes possible working quicker by an order of magnitude.

After brief drying of the slip, the small cap 12 present on the preparation 3a is pulled off from this, sintered and infiltrated in known manner in order that the necessary strength is achieved.

The above-described arrangement according to the invention, consisting of a per se known CNC milling machine, combined according to the invention with a pipette-like dosing device, can, furthermore, be used for the production of a complete ceramic crown. For this purpose, the finished small cap is, after the infiltration, again placed on the preparation 3a. The space previously taken up by the shrink-fitted film can be replaced by wax or a similar material so that a secure hold is ensured. The ceramic material is—like the slip previously on the film—applied to the small cap, whereby the control of the application pipette takes place by means of digitally stored values which correspond to the desired anatomical shape of the crown. For this purpose, previously on the preparation 3a is stuck a model of the tooth, for example of wax, the surface of which is stored in the already described way. In the case of this material application, the shrinkage of the ceramic in the case of baking is, of course, to be calculated in.

The application of the cermic material can take place from several application pipettes which contain material of differing colour shades. By means of appropriate coating and control, the desired colour shade of the crown can be so adjusted. This controlling can take place via the adjustment of the pressing out force in the pipette or via the piston advance, as well as plotted by the calculation in 3D graphics.

Furthermore, it is important in the process according to the invention that the film can be pulled on quickly and crease-free.

Figure 3:
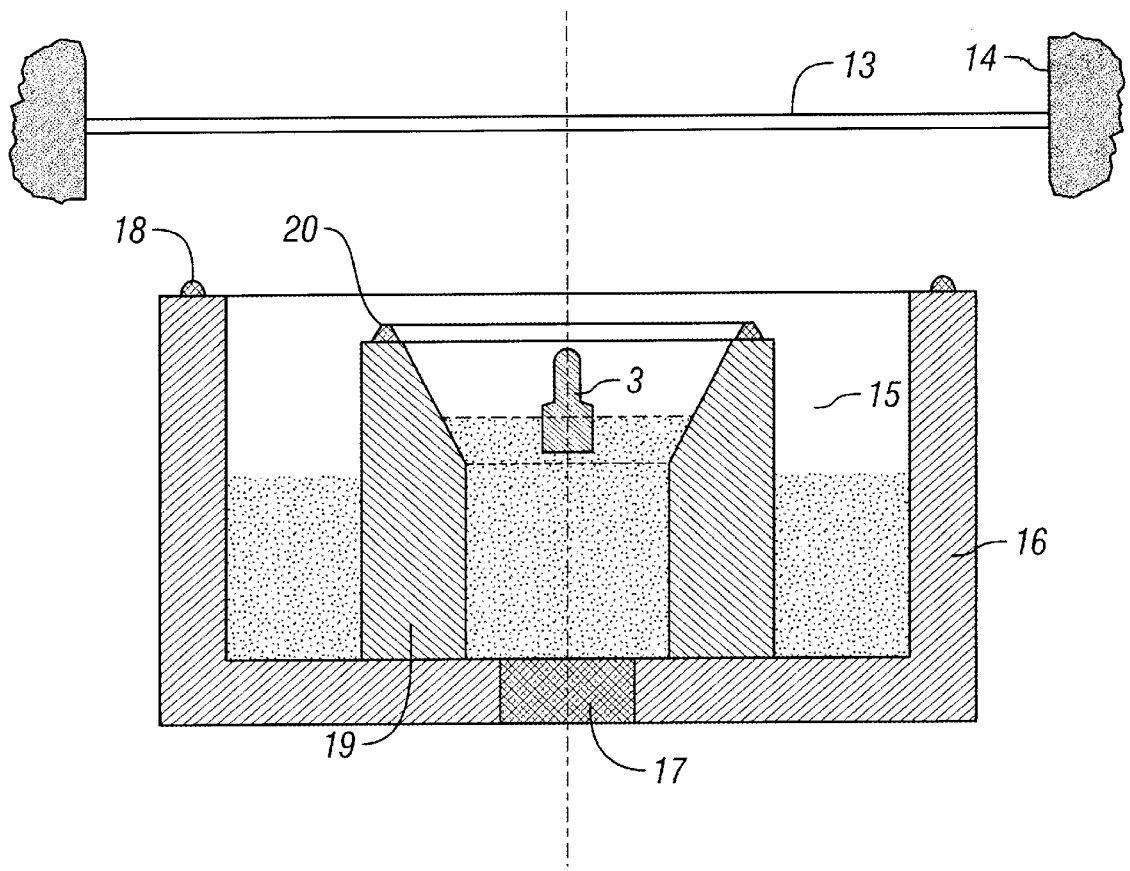
FIG. 3 a device for the rapid and crease-free shrink-fitting of a film on an individual die.

From FIG. 3, the basic construction of a deep-drawing device can be seen which fulfils the above requirements. A film is held by a clamping device 14. Since the film, after the heating, rapidly loses the heat because of its small mass, usually (not shown) heat storage elements are provided. In a granulate reception space 15, which is formed by a wall 16, is present the granulate for the holding of the object, here the single die 3. In the bottom of the reception space 15 is provided a filter 17 which prevents the granulate being sucked out by the vacuum below the filter.

The heated film is laid on the sealing lip 18 and deep drawn. It hereby encases the single die 13. Up to here, there is no difference between the invention and the prior art.

However, for the desired precision, such a device is not yet suitable. On the one hand, in the case of the above mentioned process, a very thin film is needed. Its thickness amounts to 0.1 mm or thinner for the coating of individual dies for the slip technique and at most 0.6 mm for the telescope crown technique. Such films inevitably tear in the conventional deep-drawing devices.

By the use of the funnel 19 according to the invention, which can be provided with a sealing lip 20 on the upper edge, in surprising way the tearing of the film is prevented and a crease-free covering on the individual die is achieved since, in the case of deep drawing, the funnel definably guides the film on the die whereby a uniform material thickness on the die is achieved. A further problem in the case of thin films can arise due to the granulate which usually consists of lead in cylindrical form with a diameter of about 0.5 mm.

It has now been found that brass spheroids with a diameter of 0.2 to 0.5 mm, preferably of 0.3 mm, are especially suitable since they do not perforate the film.

After the shrink fitting of the film, it is advantageous to remove the film in a limited region at the tip of the die. The small cap in the finished state of the tooth hereby lies directly on the tooth stump whereby stresses in the tooth construction are reduced.

The space which, in the case of this process, is filled by the film has the function of a place holder which is desired in the case of crowns and in bridge technology since this ensures the flow-off of the cementing material. In the case of the production of inlays, partial crowns and frames for implants and/or suprastructures, such a place holder function is not necessary but rather undesired since these tooth-prosthetic parts are to contact directly with their partner part. Therefore, one here speaks of an adhesive cementing. However, especially in the implant technology, no play is desired since this can be the cause of the falling out of the implants since usually the crowns are screwed with the implant and the appearance of a bending moment leads to the breaking of the crown.

In the case of the development of the invention, it was initially an object to replace the film by an extremely thin material which no longer showed the undesired place holder property. In extremely surprising way, the inventor has now found that commercially available lip care products, such as Labello (registered trade mark of the firm Beiersdorf AG), are best suited. For this purpose, the material must be applied to the die warm, thus above 45° C., since a very thin film can so form. Because of the poor visibility of the film due to its small thickness and/or for the improvement of the reflection of the laser beam, the colouring of the agent is recommended.

After the cooling, the die is then covered with a film which is not destroyed in the case of the application of the slip and on which the slip adheres well. After removal from the working model, the moulded blank is sintered. The separating agent according to the invention hereby again liquefies and is initially absorbed by the ceramic as by a sponge and subsequently burnt without residue in the case of the high sinter temperature. The desired precision is hereby achieved.

The so produced restoration is, therefore, best suited for the adhesive cementing and especially for the implant technology.

In the case of the production of artificial teeth or the like, as previously the ceramic mass is applied in the form of a slip with a brush by hand to the object. This technique hardly differs at all from the technique of a painter who applies from a colour pallet with the brush oil colours to a picture except that a tooth technologist normally uses a glass plate. Since slips consist of a mixture of ceramic powder and usually water, the water evaporates from the mixture, whereby the slip becomes useless since too viscous. Especially in the case of alumina slips, the water ratio is a very critical value. In the case of non-optimal water ratio, in the case of baking a very poor structure and thus a low break strength is obtained. Since this is known to the tooth technologist, to the slip present on the working glass plate, he applies a moisture storer, e.g. moist paper spheroids etc. In this point, no limits are placed on the phantasy.

On the other hand, however, the danger exists that, due to the necessary washing out of the brush, too much water is introduced into the slip. In end effect, this also has the same negative results.

The application device shown in FIG. 4 ensures a constant liquid/ceramic powder ratio in the case of the working.

The application device consists of an outer tube 21 which, in the case of use, lies like a brush in the hand of the tooth technologist. Into the outer tube 21 is introduced an elastic inner tube 23, preferably of silicone rubber, which is filled with the ceramic mass. Outer tube 21 and inner tube 23 taper to an application tip 24. Since the inner space of the application device is closed by a cap 25, by exertion of a finger pressure over the finger pressure opening 26, an underpressure is achieved which permits the slip to emerge at the application tip 24. In order to remove an underpressure which arises in the case of the going back of the pressed-in inner tube 23 into the normal position, a venting valve 27 can be provided.

For the adaptation to the particular working conditions, the application tip can be slit like a fountain pen or formed like a brush. The form of the tip depends upon the viscosity of the slip.

Since the elastic inner tube 23 can be pushed into the outer tube 21, it is possible to mix the slip at the producer of the ceramic powder and to have it filled into the inner tube 23 since, in the case of the mixing in the dental laboratory, false mixing ratios are easily possible. In order to obtain a slip ready for use, the inner tube has only then to be cut off at both ends or opened in some other way.

In comparison with other conceivable devices, this construction has the advantage that no mechanical parts, such as pistons, are needed.

Figure 5:
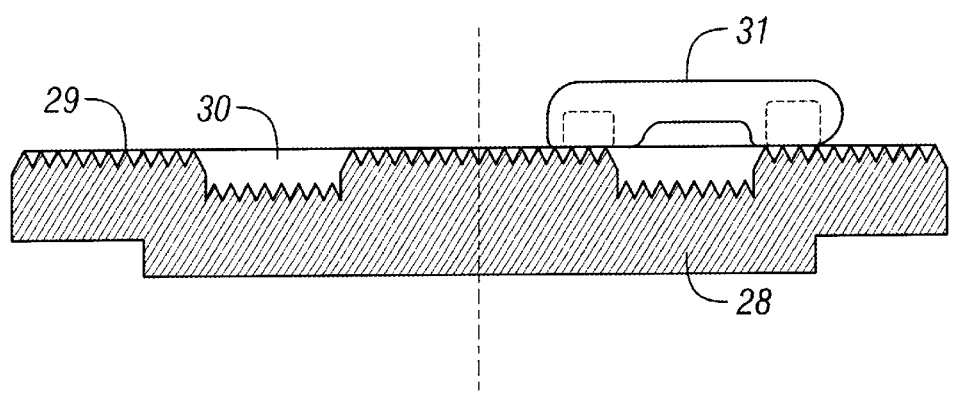
FIG. 5 a substrate for frames during the infiltration procedure.
Figure 6A:
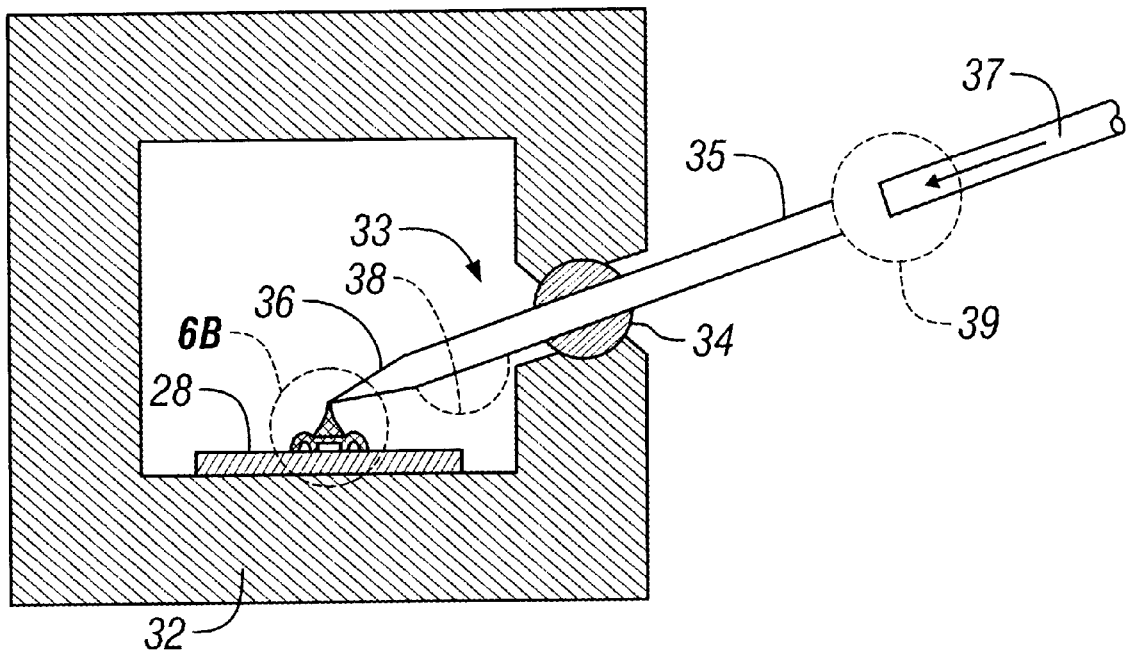
FIG. 6 a device for the infiltration of the pre-sintered frame with glass.
Figure 6B:
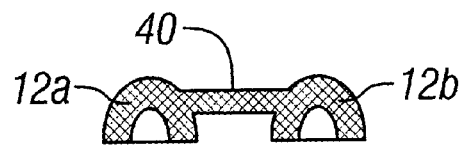

A further acceleration of the process is achieved with the devices according to FIGS. 5 and 6.

Hitherto, during the infiltration, the frame was laid on a platinum foil. Platinum is not moistened by molten glass. Since, in principle, one must work with an excess of infiltration powder, the excess glass flows off on the surface of the frame on to the platinum foil and there forms a glass foot on the edge of the frame which must be removed by laborious detailed work by grinding and/or sand blasting. Under certain circumstances, a part of the excess glass must be removed by heating again. Besides the considerable expenditure of labour, the danger also exists that the frame is damaged in the case of this work.

With the device according to FIG. 5, a rapid and sure removal of the excess glass is ensured.

FIG. 5 shows a substrate 28 which, in the present case, is formed rotation symmetrically, which simplifies its production. The surface of the substrate 28 has a profiled surface structure in the form of a zig-zag profiling 29. Any other profiling is more or less equally well suited. All that is important is that the raised regions are not too great in comparison with the frame. Furthermore, the substrate 28 has a groove which is bridged by a bridge member frame 31 laid thereon. The substrate 28 consists of a porous material which is moistened by glass. Thus, in this point, the opposite to the prior art is required which starts from non-moistenable platinum. As material, especially embedding masses have proved useful which are usual in dental technology. However, in principle, any ceramic material is moistenable by glass and therefore suitable.

During the heating procedure, the excess glass flows off on the bridge 31 and drops, on the one hand, into the groove 30 and is, on the other hand, absorbed by the porous surface. Precisely for bridges with large material mass in the middle part, the possibility of the dropping off is of advantage since the dropped off glass no longer displays a binding with the bridge. The amount of glass later to be removed is hereby minimised.

Since, in the case of the penetration of the liquid glass into the porous material of the substrate, a mixed material of glass and ceramic is formed, the excess glass still hanging on the frame shows weak strength values in comparison with pure glass. It can thus be easily and rapidly mechanically removed.

Also in the case of the lifting off of the substrate, no damage of the frame is possible since the indentations shown in the Figure simply break off from the substrate without a particularly strong force being necessary when the substrate consists of an embedding mass or the like.

In FIG. 6 is schematically shown a conventional ceramic baking oven which is present in dental laboratories. Through the wall of the oven 32 is passed in a pipette-like application device 33 movable from the outside which is expediently mounted in a ball joint 34. In the illustrated case, the application device consists of a platinum tube 35 with a tip 36. Since the tube 35 is displaceably mounted within the ball joint 34, the application tip 36 is three-dimensionally movable inside of the oven 32.

In the following is described the production according to the invention of a frame for a bridge.

According to the previously described foil process are first produced two small caps 12a and 12b from a ceramic slip which are bound with a bridge intermediate member 40 of the same material, e.g. alumina. The bridge intermediate member can be produced manually but also mechanically in that the position of the two small caps 12a and 12b is measured on the working model and then milled out computer-controlled from a pre-sintered moulded blank. The frame is subsequently sintered. If the so-produced bridge frame were glass-infiltrated according to the prior art, at this point of time one would a) cool the oven, b) remove the bridge frame, c) apply the infiltration glass in the form of powder and d) again heat the powdered frame for the melting of the glass. As infiltration glass, one usually uses a glass frit which is already known from EP-A-0030851 or glass with high lanthanum content. That these steps are involved with energy and time losses was recognised as a foundation of the invention.

Therefore, the first step lies in that the frame remains in the oven without cooling, the best on a substrate 28 according to FIG. 5.

During and/or immediately after the sintering, the infiltration glass is melted in the oven 32 itself in that into the tube 35 is introduced a glass rod 37 which first becomes liquid at the tip 36. By corresponding further pushing of the rod 37, a sufficient possibility of dosing is given until the frame is fully coated with infiltration glass. After about 4 hours at about 1100° C., the infiltration procedure is concluded. The process can be observed through a non-shown fire-proof glass window.

The use of a finished glass rod instead of glass powder has the advantage that the laborious production of glass powder can be omitted.

The melting of powder in a platinum tube is, namely, not quite problem-free since liquid glass does not moisten platinum and, consequently, no capillary effect is present in the tube. The glass would, therefore, simply flow out of the tube if no special precautions had been made. Such a precaution would be the indicated small chamber 38 in which, in horizontal position of the tube, the glass powder can be melted without glass flowing out. In tilted position of the tube, by means of the indicated bellows 39, the glass can be dosed.

Furthermore, it is also to be observed that platinum and other suitable metals have a high heat conductivity which make necessary non-indicated insulation measures in order that the tube 35 can be handled.

After ending of the infiltration and the usual mechanical after-working, in a further sinter procedure, the facing ceramic is applied to the bridge frame.

With the present invention is thus provided a further breakthrough for the production of fully ceramic restorations which, on the one hand qualitatively meet all requirements of a tooth replacement, on the other hand, because of the efficiency of the process, are extremely cost-favourable. In this regard, the invention fulfils a social requirement.

REFERENCE LIST 1 motor
2 rod
3 die
3a preparation of the die
4 adhesive wax
5 application tool
6 shrink-fitted film
7 blow drier
8 laser
9 application device for slip
10 milling head
11 milling machine
12 small cap
13 film before the shrink fitting
14 fixing device
15 granulate reception chamber
16 wall
17 filter
18 1st sealing lip
19 funnel
20 2nd sealing lip
21 outer tube
22 ceramic mass
23 inner tube
24 application tip
25 cap
26 finger pressure opening
27 ventilation valve
28 substrate
29 profiling
30 groove
31 bridge member frame
32 ceramic oven
33 application device for infiltration glass
34 ball joint
35 platinum tube
36 tip
37 glass rod
38 melting chamber
39 blowing bellows
40 bridge intermediate member

What is claimed is:

1. A process for the production of one of a fully-ceramic inlay, crowns, bridge, partial bridge or frames for an implant or superstructure in dentistry, comprising producing a frame from a ceramic by shrink-fitting on a die of a working model a film; or covering the die of the working model with a separating agent which is liquid at temperatures above 45° C. and which, at room temperature, has a lipstick consistency;

applying a slip to the shrink-fitted film or separating agent;

removing the slip present on the film or separating agent from the working model;

after the separation from the working model, baking the slip material; and, after baking to produce the frame in the form of a resulting mold blank, infiltrating the blank with glass, wherein during the slip application, the die is fixed on a rotating rod, of a computer numerical control milling machine, and further comprising
sensing the surface profile of the die
storing this profile,
controlling a dosing device via the stored data,
applying the slip uniformly on the film or separating agent and subsequently milling off the applied slip material by means of the stored data to a desired thickness.

2. A process according to claim 1, comprising deep drawing the film on a single die by holding the die in a granulated bed;

applying a vacuum below the die; and shrink-fitting a heated film onto the die,
wherein the die, inside the granulate bed, is surrounded by a funnel for guiding the film onto the die.

3. A process according to claim 1, comprising producing a crown by fixing the blank produced on the die present on the rotating rod;

adhering to the blank a form which corresponds to the desired anatomical form of the crown;

sensing the form;

storing data representative of the form;

after removal of this form, applying a ceramic material in the desired thickness by a computer numerical control controlled process; and baking the blank plus ceramic material to give the finished crown.

4. A process according to claim 1, wherein a separating agent layer is introduced between the film and the die.

5. A process according to claim 1, wherein said frame is a sintered frame and wherein said infiltrating comprises infiltrating the frame by placing the frame, during heating, on a porous substrate wettable by liquid glass, which absorbs the excess glass.

6. A process according to claim 1, comprising, for the infiltration in a ceramic oven, of the sintered frame without removal of the frame from the ceramic oven, melting a glass mass on during and/or after sintering, in an application device present in the ceramic oven, and applying the liquid glass by the application device to the frame.

7. A process according to claim 6, comprising providing the glass in the form of a glass rod.

8. A process according to claim 6, wherein the ceramic oven includes a pipette-like application device movable from the outside, which is three-dimensionally movable and wherein said applying comprises applying with said pipette-like application device.

9. A process according to claim 8, wherein said applying comprises applying with an application device that is mounted in a ball joint in a wall of the ceramic oven and that has on one end a pointedly running tube.

10. A process according to claim 9, wherein said applying comprises applying with an application device that comprises an outer tube in which is placed an elastic inner tube, whereby the outer tube is provided with a finger opening and the elastic inner tube tapers on the end to an application tip and the other end is closed off to the atmosphere.

11. A process according to claim 1, whereby the rotating rod is a shaft driven by a motor with regulatable speed of rotation; and further comprising drying the slip applied to the die with a blow drier with adjustable air temperature.

* * * * *